United States Patent [19]
Nishiguchi et al.

[11] Patent Number: 6,046,040
[45] Date of Patent: Apr. 4, 2000

[54] METHOD FOR PRODUCING GLYCOCONJUGATES

[75] Inventors: Susumu Nishiguchi; Yoshihiko Maekawa, both of Ohtsu; Shin-ichiro Nishimura, Sapporo; Kuriko Yamada, Ishikari, all of Japan

[73] Assignee: Toyo Boseki Kabushiki Kaisha, Osaka, Japan

[21] Appl. No.: 09/123,766

[22] Filed: Jul. 28, 1998

[30] Foreign Application Priority Data

Jul. 29, 1997 [JP] Japan ................................. 9-203443

[51] Int. Cl.⁷ ..................... C12P 19/18; C12P 19/14; C12P 19/00; C12P 19/26; C12P 7/64
[52] U.S. Cl. ..................... 435/97; 435/99; 435/100; 435/101; 435/74; 435/72; 435/134; 435/135; 435/174; 435/176; 435/177; 435/84
[58] Field of Search .................. 435/97, 99, 100, 435/101, 74, 72, 134, 135, 174, 176, 177, 84

[56] References Cited

U.S. PATENT DOCUMENTS

| | | | |
|---|---|---|---|
| 4,593,004 | 6/1986 | Boross et al. | 435/181 |
| 5,288,637 | 2/1994 | Roth | 435/288 |

OTHER PUBLICATIONS

Nishimura et al, Tetrahedron Letters 35(31):5657–5660, 1994.
Nishimura et al, J. Am. Chem. Soc. 119(43):10555–10556, 1997.
David et al, Pure Appl. Chem. 59(11):1501–1508, 1987.
Trinchera et al, J. Biol. Chem. 266(31):20907–20912, 1991.

*Primary Examiner*—Francisco Prats
*Attorney, Agent, or Firm*—Kenyon & Kenyon

[57] ABSTRACT

A method for producing glycoconjugate, which comprises the steps of:

(i) binding a sugar residue to the side chain of a water-soluble polymer via a linker having a selectively cleavable linkage to give a primer, and bringing said primer into contact with an immobilized glycosyltransferase in the presence of a sugar nucleotide, to transfer a sugar residue of said sugar nucleotide to the sugar residue of said primer, (ii) elongating a sugar chain by transfer of plural sugar residues by repeating the step (i) at least once, (iii) removing, where necessary, a by-produced nucleotide or an unreacted sugar nucleotide, and (iv) repeating the steps (i)–(iii) where necessary and releasing the glycoconjugate by selectively cleaving the cleavable linkage in the linker, from the above-mentioned primer connecting the sugar chain elongated by the transfer of plural sugar residues, and a method for producing a sphingoglycolipid.

8 Claims, 2 Drawing Sheets

METHOD FOR PRODUCING GLYCOCONJUGATES

TECHNICAL FIELD OF THE INVENTION

The present invention relates to a method of producing glycoconjugates having an optional sugar chain structure, such as oligosaccharides, glycopeptides and glycolipids, specifically sphingoglycolipids, that utilizes an immobilized glycosyltransferase.

BACKGROUND OF THE INVENTION

While saccharride is a major component constituting a living body together with nucleic acid and protein, its structure and function are not known as clearly as those of nucleic acid and protein. Carbohydrate generally forms a polymer having sugar chains in sequence and binds with protein and lipid to form a pronouncedly complicated complex molecule generally referred to as a glycoprotein, glycolipid or proteoglycan. While nucleic acid and protein are polymers wherein constituent units of nucleotide and amino acid are linearly bonded, the structure of the sugar chain is far more complicated than nucleic acid and protein, as its molecule contains plural branches and the constituent unit monosaccharide binds in a variety of manners. Such complicated structure of the saccharide is one of the major causes of the delay in the study of saccharide.

Along with the elucidation of the saccharide's role in cell recognition, immunity, differentiation, fertilization, senescence, malignant alteration and the like in recent years, saccharide has become a target of study that attracts significant attention. Under the circumstances, many attempts have been made to synthesize a sugar chain having a natural structure or a novel sugar chain. As regards nucleic acid and protein, automatic synthesis techniques have been already established, and these techniques have obviously accelerated the progress of the researches in these fields. An automatic synthesis technique for a sugar chain has been eagerly desired, but effective methods of various protection and deprotection and a method to achieve a high yield, steroselective glycosylation reaction have not been developed to satisfaction, and thus, the desired technique has not been available.

Recently, Danishefsky et al. proposed a solid phase synthetic method of saccharide utilizing glycal (Science, 260, 1307 (1993)), and this has led to the resolution of the problems as to the high yield and steroselective glycosylation to a certain extent. This method comprises (i) binding a glycal to a polystyrene-divinylbenzene copolymer via a diphenylsilyl group to allow reaction between said glycal and 3,3-dimethyldioxirane, that converts glycal to a 1,2-anhydrosugar, and (ii) using this anhydrosugar as a sugar donor, reaction with a different glycal suitably protected to form a glycoside glycal, and these steps are repeated. According to this method, a new glycosidic linkage can be stereoselectively formed, but only a compound that has a glycosidic linkage at the trans-position with respect to the 2-position hydroxy of the donor can be formed.

Meanwhile, a solid phase synthetic method of a sugar chain has been proposed, that utilizes glycosyltransferase capable of stereoselectively forming a glycosidic linkage without any protection. This method has not been further developed, due to the fact that the available glycosyltransferase is limited in kind and is expensive. In recent years, however, genes of various glycosyltransferases have been isolated and a large-scale production of glycosyltransferase by genetic recombination techniques has become possible.

For example, U. Zehavi et al. have reported on a solid phase synthesis method by glycosyltransferase using a polyacrylamide gel bound with an aminohexyl group as a solid phase carrier (Carbohydr. Res., 124, 23 (1983), Carbohydr. Res., 228, 255 (1992)). This method comprises the steps of converting a suitable monosaccharide to 4-carboxy-2-nitrobenzylglycoside, condensing this glycoside with amino group of the above-mentioned carrier, elongating the sugar chain by glycosyltransferase using the condensate as a primer, and releasing the oligosaccharide by photolysis. According to this method, however, sugar transfer yield is low and is less than 10%.

It has been a common understanding that glycosyltransferase does not react well with saccharide or oligosaccharide bound to a solid phase carrier, and efficient elongation of sugar chain is difficult to achieve. A recent report has documented that linkage between 4-carboxy-2-nitrobenzylglycoside and solid phase carrier by a linker having a long chain, such as hexamethylene and octamethylene, led to an improved sugar transfer yield at the maximum of 51% (React. Polym., 22, 171 (1994), Carbohydr. Res., 265, 161 (1994)).

C. -H. Wong et al. have documented a report wherein a sugar chain is elongated using a glycosyltransferase and aminated silica bound with the following group of (a) as primers, and the elongated sugar chain is cleaved out utilizing hydrolysis of α-chymotrypsin (J. Am. Chem. Soc., 116, 1136 (1994)). By this method, the transglycosylation yield was 55%. C. -H. Wong et al. revised the group to be bonded to the solid phase carrier to the following (b) and reported a method wherein the sugar chain was elongated by glycosyltransferase and released by hydrazinolysis, whereby the transglycosidation proceeded almost quantitatively (J. Am. Chem. Soc., 116, 11315 (1994)).

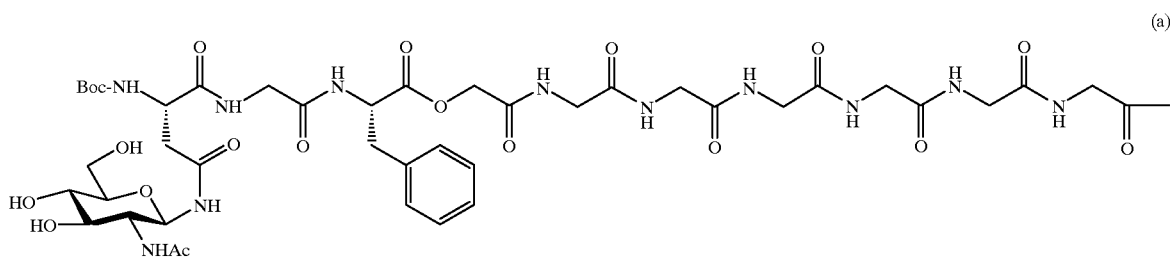
(a)

wherein Boc is t-butoxycarbonyl and Ac is acetyl.

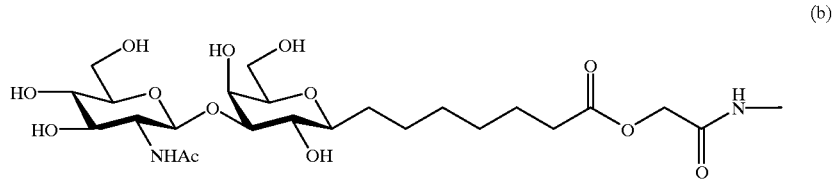
(b)

wherein Ac is acetyl.

As another method, M. Meldal et al. have reported a method comprising elongation of sugar chain using glycosyltransferase and, as a primer, a polymer of mono- and diacryloyl compound of diaminated poly(ethylene glycol), the polymer having a group of the following formula (c) bonded thereto, and release of the sugar chain by trifluoroacetic acid, wherein the transglycosidation proceeded almost quantitatively (J. Chem. Soc., Chem. Commun., 1849 (1994)).

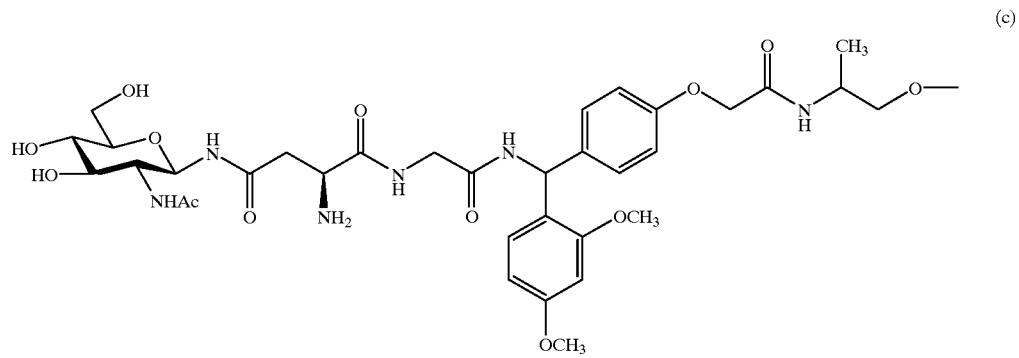
(c)

wherein Ac is acetyl.

As mentioned above, when sugar chain is elongated by glycosyltransferase on a solid phase carrier, the kind of group (linker) which connects the solid phase carrier to the sugar residue (receptor of initial transglycosylation) varies transglycosylation yield. When the sugar chain is liberated from the carrier, the presence of a specifically cleavable bond in the linker is markedly advantageous.

In sugar chain elongation by glycosyltransferase, the use of an immobilized glycosyltransferase that permits repetitive use is desirable, since glycosyltransferase is highly expensive, though a large-scale production by genetic recombination techniques is becoming available. It should be noted that the above-mentioned methods are associated with a drawback that an immobilized glycosyltransferase cannot be used due to the sugar chain elongation on an insoluble carrier.

It is necessary to carry out the sugar chain elongation not on an insoluble carrier but on a water soluble carrier, if an immobilized glycosyltransferase is to be used.

As a sugar chain synthetic method using a water soluble carrier, the present inventors have reported a method comprising elongation of a sugar chain using a glycosyltransferase and, as a primer, a polyacrylamide having a group of the following formula (d) bonded to the nitrogen atom of the amide moiety, and cleavage of the elongated sugar chain by hydrolysis of α-chymotrypsin (Tetrahedron Lett., 35, 5657 (1994)). However, the glycosyltransferase also used in this method is a soluble enzyme and is not immobilized. Thus, there has been found no precedent case where a sugar chain was synthesized by an immobilized glycosyltransferase and a water soluble carrier.

(d)

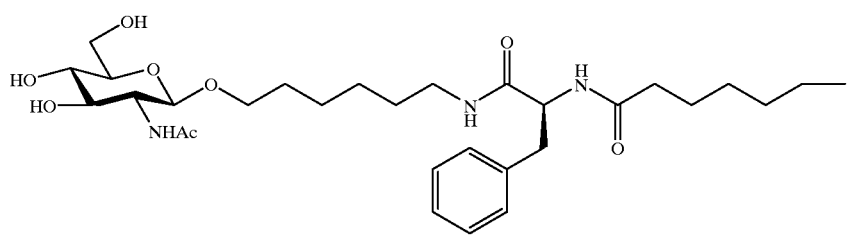

wherein Ac is acetyl.

According to C. Auge, for immobilization of a glycosyltransferase, galactosyltransferase is first immobilized on an agarose gel activated by cyanogen bromide, and oligosaccharide is synthesized (Pure & Appl. Chem., 59, 1501 (1987)). According to J. Thiem et al., galactosyltransferase is immobilized on aminopropyl silica using glutaraldehyde, and used for the synthesis of oligosaccharide (Angew. Chem. Int. Ed. Engl., 25, 1096 (1986)). However, the substrate is a typical monosaccharide or oligosaccharide in both cases, and transglycosylation to a polymer substrate having sugar chains in sequence with immobilized glycosyltransferase has not been reported. Generally, an immobilized enzyme is considered to be inferior to a soluble enzyme in the reactivity with a polymer substrate. This is attributable to the difficulty experienced by an immobilized enzyme in contacting a polymer substrate, in comparison to a soluble enzyme. Hence, an efficient elongation reaction of a sugar chain on a water soluble polymer substrate (carrier) using an immobilized glycosyltransferase will be extremely useful.

It is therefore an object of the present invention to provide a method for synthesizing a sugar chain using an immobilized glycosyltransferase.

SUMMARY OF THE INVENTION

In accordance with the present invention, the above-mentioned problems can be solved by the steps of:
 (a) binding a suitable sugar residue to a side chain of a water-soluble polymer via a linker having a selectively cleavable linkage under appropriate conditions to give a primer,
 (b) bringing said primer into contact with an immobilized glycosyltransferase in the presence of a sugar nucleotide to transfer the sugar residue from the sugar nucleotide to the primer,
 (c) repeating this transglycosidation appropriate times,
 (d) removing, where necessary, a by-produced nucleotide and an unreacted sugar nucleotide, and
 (e) selectively cleaving the cleavable linkage in the linker to release the glycoconjugate from the primer connecting the elongated sugar chain.

Hence, the present invention provides a method for producing glycoconjugate, which comprises the steps of:
 (i) binding a sugar residue to the side chain of a water-soluble polymer via a linker having a selectively cleavable linkage to give a primer, and bringing said primer into contact with an immobilized glycosyltransferase in the presence of a sugar nucleotide, to transfer a sugar residue of said sugar nucleotide to the sugar residue of said primer,
 (ii) elongating a sugar chain by transfer of plural sugar residues by repeating the step (i) at least once,
 (iii) removing, where necessary, a by-produced nucleotide or an unreacted sugar nucleotide, and (iv) repeating the steps (i)–(iii) where necessary and releasing the glycoconjugate by selectively cleaving the cleavable linkage in the linker, from the above-mentioned primer connecting the sugar chain elongated by the transfer of plural sugar residues.

The present invention also provides a method for producing a sphingoglycolipid comprising the following steps of:
 (i) binding a group of the formula (I) to the side chain of a water-soluble polymer to give a primer, and bringing said primer into contact with an immobilized glycosyltransferase in the presence of a sugar nucleotide, to transfer a sugar residue of said sugar nucleotide to the sugar residue of said primer, (I)

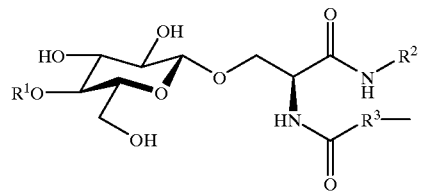

wherein $R^1$ is a β-galactose residue or H, $R^2$ is alkyl or alkenyl having 6 to 20 carbon atoms and $R^3$ is alkylene having 5 to 19 carbon atoms,
 (ii) elongating a sugar chain by transfer of plural sugar residues by repeating the step (i) at least once,
 (iii) removing, where necessary, a by-produced nucleotide or an unreacted sugar nucleotide, and
 (iv) repeating the steps (i)–(iii) where necessary, and reacting a ceramide glycanase with the primer connecting an elongated sugar chain by the transfer of plural sugar residues in the presence of a ceramide to transfer an oligosaccharide residue having the plural sugar residues to the ceramide from said primer.

DETAILED DESCRIPTION OF THE INVENTION

Figure 1:
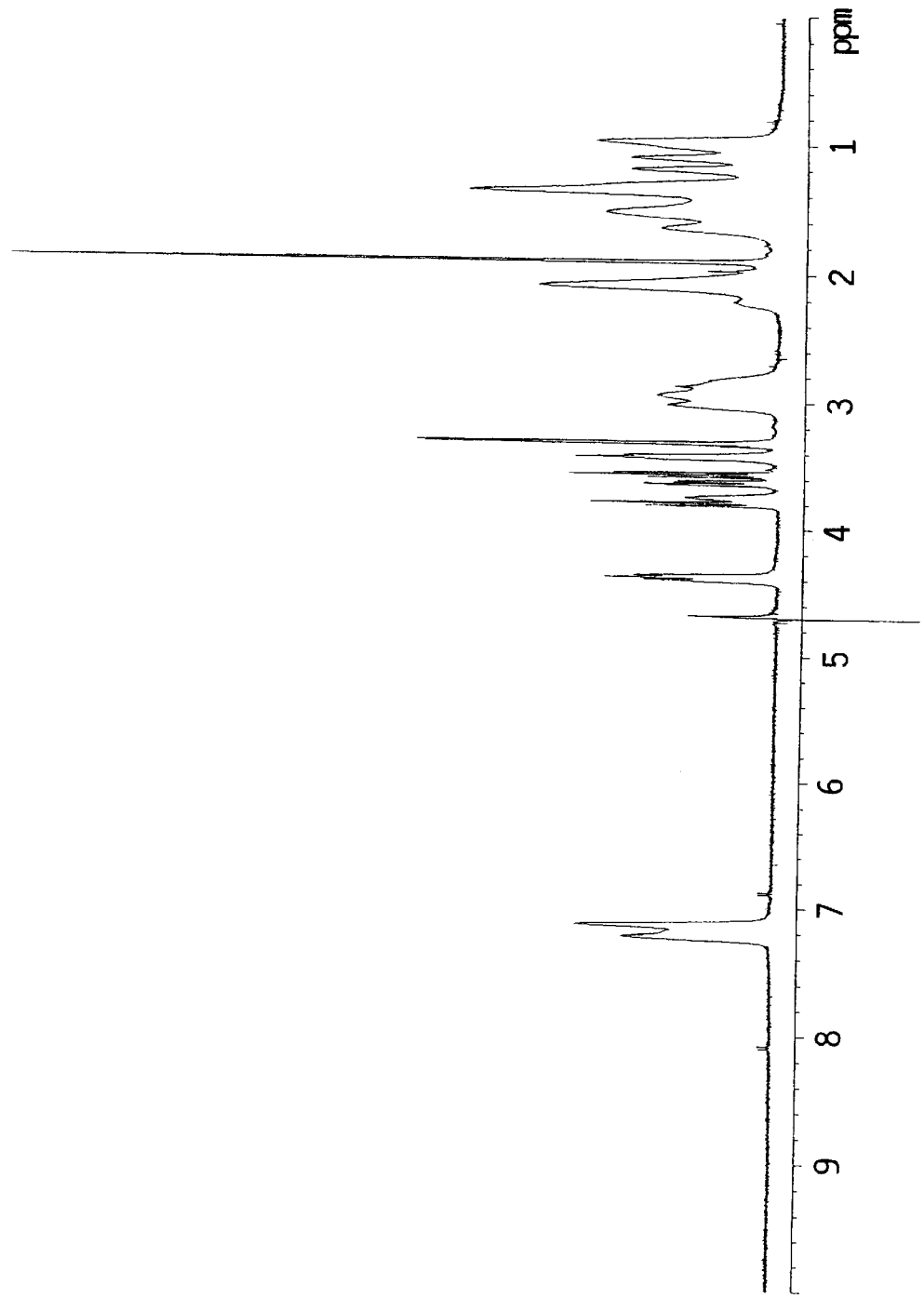
FIG. 1 is an H-NMR spectrum chart of N-(6'-acryloylaminocaproyl)-phenylalanyl-6-aminohexyl-2-acetamido-2-deoxy-β-D-glucopyranoside-acrylamide copolymer (Reference Example 7).

The primer of the present invention is a water-soluble polymer having, at the side chain thereof, a sugar residue via a linker having a selectively cleavable bond.

The water-soluble polymer to be used in the present invention may be any as long as it is a polymer soluble in aqueous media. Preferred are polymers and copolymers of acrylic or methacrylic monomers of acrylic acid, methacrylic acid, acrylamide, methacrylamide and derivatives thereof, and copolymers of these acrylic or methacrylic monomers and other vinyl compounds. The other vinyl compounds include, for example, vinyl alcohol, vinyl acetate, styrene, vinylpyridine and the like. In addition, vinyl polymers and copolymers of poly(vinyl alcohol), poly (ethylene glycol), polypropylene glycol and the like can be used.

In the present invention, the side chain of water-soluble polymer refers to the part other than the polyalkylene chain formed by polymerization of the above-mentioned water-soluble polymers. In the case of polyacrylamide, for example, the side chain is —$CONH_2$.

In the present invention, by the selectively cleavable bond is meant a bond which can be cleaved, under the conditions free from cleavage or isomerization of the glycosidic linkage of sugar chain elongated by glycosyltransferase. The cleavage of the linkage results in release of the glycoconjugate from a water-soluble polymer. Examples of such linkage include one capable of being cleaved in a weak acidic or weak alkaline environment, one capable of being cleaved by catalytic reduction, one capable of being cleaved by photo-reaction and one capable of being cleaved by enzyme such as protease and ceramide glycanase. Of these, the linkage capable of being cleaved by enzyme, such as protease and ceramide glycanase, is preferable, in view of specificity of reaction and easiness.

A selectively cleavable linkage, such as an ester linkage of phenylalanine alkyl ester, can be selectively cleaved by α-chymotrypsin. The glycosidic linkage of O-glycosyl-N-acylserinealkylamide can be selectively cleaved by ceramide glycanase.

Ceramide glycanase can transfer, in the presence of ceramide, monosaccharide or oligosaccharide linked to serine residue to the 1-hydroxy of said ceramide.

In the present invention, the linker containing a selectively cleavable linkage means a functional group capable of forming chemical bond at the both ends, such as hydroxy, amino, carboxy, thiol group and the like. It is linked to the functional group of the side chain of a water-soluble polymer and hydroxy of sugar chain via the functional group of the linker, and contains a selectively cleavable linkage mentioned above in said molecule.

In the present invention, the sugar residue to be linked to the side chain of a water-soluble polymer via a linker may be any as long as it can be a receptor of glycosyltransferase, and is exemplified by glucose residue, galactose residue, N-acetylglucosamine residue, N-acetylgalactosamine residue, mannose residue, glucuronic acid residue, lactose residue and the like.

The primer is explained in detail in the following by referring to an example wherein a group of the formula (I) or (II) is linked to the nitrogen atom of the amide moiety of polyacrylamide.

(I)

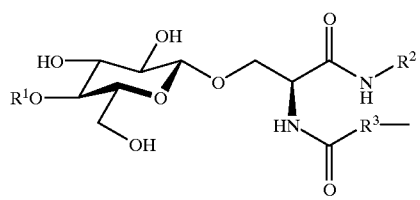

wherein $R^1$ is β-galactose residue or H, $R^2$ is alkyl or alkenyl having 6 to 20 carbon atoms and $R^3$ is alkylene having 5 to 19 carbon atoms.

(II)

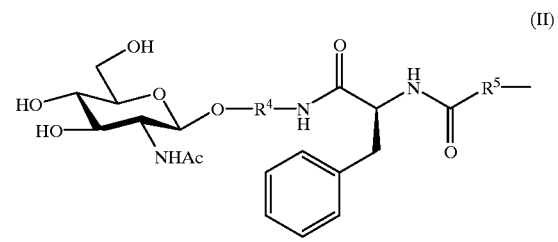

wherein $R^4$ is alkylene having 2 to 20 carbon atoms, $R^5$ is alkylene having 5 to 19 carbon atoms and Ac is acetyl.

Alkyl having 6 to 20 carbon atoms at $R^2$ is exemplified by hexyl, octyl, dodecyl, octadecyl and the like, and alkenyl having 6 to 20 carbon atoms is exemplified by cis-9-octadecenyl and the like.

Alkylene having 5 to 19 carbon atoms at $R^3$ is exemplified by pentylene, heptylene, nonylene, heptadecylene and the like.

Alkylene having 2 to 20 carbon atoms at $R^4$ is exemplified by ethylene, butylene, hexylene, dodecylene, octadecylene and the like.

Alkylene having 5 to 19 carbon atoms at $R^5$ is exemplified by pentylene, heptylene, undecylene, heptadecylene and the like.

The primer to be used in the present invention may be a combination of $R^1$, $R^2$ or $R^3$, or a combination of $R^4$ and $R^5$.

The group of the formula (I) is exemplified by the groups of the following formulas (e), (f) and (g).

(e)

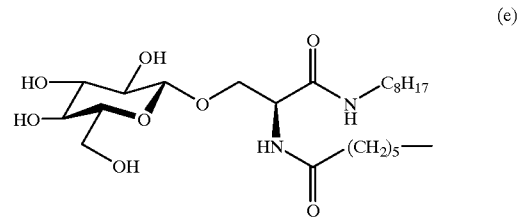

(f)

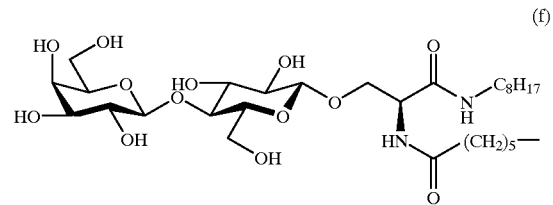

(g)

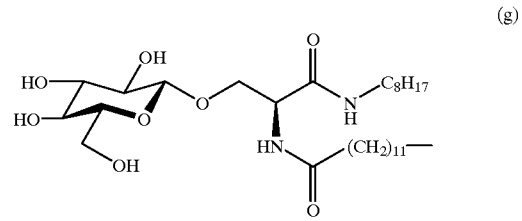

The group of the formula (II) is exemplified by the groups of the following formulas (h), (i) and (j).

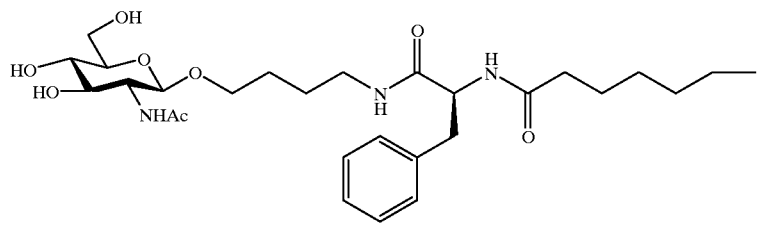

(h)

wherein Ac is acetyl,

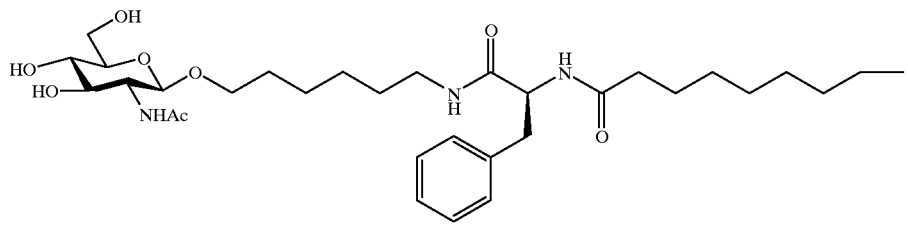

(i)

wherein Ac is acetyl,

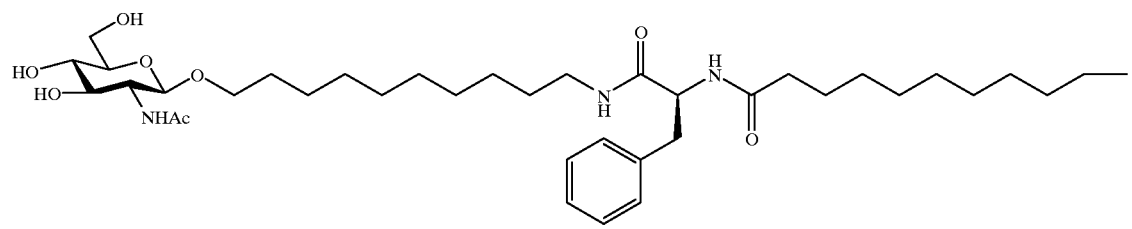

(j)

wherein Ac is acetyl.

In the present invention, the primer of the present invention can be produced by copolymerization of a polymerizable monomer having a sugar residue and represented by the formula (III) or (IV) and acrylic monomer or methacrylic monomer using polymerization initiator, for example, a radical initiator such as ammonium persulfate and potassium persulfate.

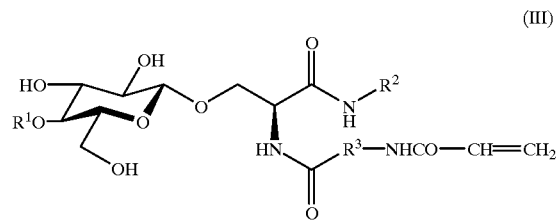

(III)

wherein $R^1$, $R^2$ and $R^3$ are as defined above,

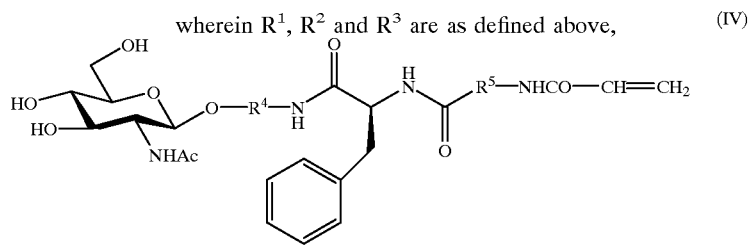

(IV)

wherein $R^4$, $R^5$ and Ac are as defined above.

The polymerizable monomer of the formula (III) can be prepared by the following procedures:
(a) condensation of activated sugar of the formula (V) with a serine derivative of the formula (VI) in the presence of suitable catalyst,
(b) removal of the amino-protecting group at the serine residue moiety,
(c) condensation with acrylamide derivative of the formula (VII), and
(d) removal of the protecting group of the sugar moiety.

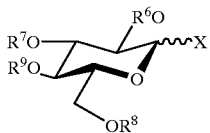

(V)

wherein $R^6$, $R^7$ and $R^8$ are each independently acyl-protecting group or ether-protecting group, $R^9$ is β-galactose residue wherein hydroxy is protected by acyl-protecting group or ether-protecting group, acyl-protecting group or ether-protecting group and X is activated group,

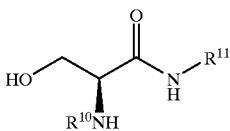

(VI)

wherein $R^{10}$ is a protecting group and $R^{11}$ is alkyl or alkenyl having 6 to 20 carbon atoms, $$CH_2=CH-CONH-R^{12}-COY \quad (VII)$$

wherein $R^{12}$ is alkylene having 5 to 19 carbon atoms and Y is hydroxy, bromine atom or chlorine atom.

In the formula (V), the acyl-protecting group is exemplified by acetyl, benzoyl and the like, and ether-protecting group is exemplified by benzyl, p-methoxybenzyl, allyl and the like.

The activated group at X is exemplified by bromine (Br), fluorine (F), trichloroacetoimidate and the like.

The activated sugar of the formula (V) can be synthesized by a conventional chemical reaction. Examples thereof include 2,3,4,6-tetra-O-acetylglucosyl bromide and 2,3,6,2',3',4',6'-hepta-O-acetyllactosyl bromide.

In the formula (VI), the protecting group is exemplified by benzyloxycarbonyl, t-butoxycarbonyl, 9-fluorenylmethyloxycarbonyl and the like. The alkyl having 6 to 20 carbon atoms at $R^{11}$ is exemplified by hexyl, octyl, dodecyl, octadecyl and the like, and alkenyl having 6 to 20 carbon atoms at $R^{11}$ may be, for example, cis-9-octadecenyl and the like.

The serine derivative of the formula (VI) may be, for example, N-benzyloxycarbonylserineoctylamide, N-(9-fluorenylmethyloxycarbonyl)-serinestearylamide and the like.

The catalyst to be used for the condensation of an activated sugar with a serine derivative can be appropriately selected depending on the activated group X. When the activated group is bromine (Br), for example, a salt of heavy metal such as silver, mercury and the like, quaternary ammonium salt and the like may be used. When it is fluorine (F), a combination of tin chloride (II) and a silver salt, a zirconocene complex, a hafnocene complex, trimethylsilyl trifluoromethanesulfonate and the like may be used. When it is trichloroacetoimidate, $BF_3OEt_2$, trimethylsilyl trifluoromethanesulfonate and the like may be used.

This condensation reaction is often carried out under anhydrous conditions in the presence of molecular sieves or anhydrous calcium sulfate.

The solvent is appropriately selected depending on the substrate (e.g., activated sugar and serine derivative) to be used, and examples thereof include hydrocarbon halide such as dichloromethane and 1,2-dichloroethane, aromatic hydrocarbon such as toluene and benzene, and diethyl ether.

The reaction temperature is generally about −70° C.–100° C., in view of the reactivity of the activated sugar, which is preferably as low as possible as long as the reaction is not adversely affected.

The amino-protecting group at the serine residue moiety can be removed by a method appropriately selected depending on the kind of protecting group. When it is benzyloxycarbonyl, for example, hydrogenolysis is used; when it is t-butoxycarbonyl, HBr/acetic acid or HF is used; and when it is 9-fluorenylmethyloxycarbonyl, a treatment with a base such as diethylamine is used.

In the formula (VII), alkylene at $R^{12}$ and having 5 to 19 carbon atoms is exemplified by pentylene, heptylene, nonylene, heptadecylene and the like.

The condensation with an acrylamide derivative of the formula (VII) is generally carried out using a condensing reagent such as carbodiimide, N-ethoxycarbonyl-2-ethoxy-1,2-dihydroquinoline and the like.

The protecting group at the oligosaccharide moiety can be removed by a method appropriately selected depending on the kind of the protecting group. For example, acetyl and benzoyl can be removed by sodium methoxide in methanol; benzyl can be removed by hydrogenolysis; p-methoxybenzyl can be removed by hydrogenolysis or oxidizing agent such as 2,3-dichloro-5,6-dicyano-p-benzoquinone and ammonium cerium nitrate; and allyl can be removed by isomerization to propenyl with potassium t-butoxide or a Wilkinson complex, followed by a treatment with an acid, mercury salt or iodine.

The polymerizable monomer of the formula (IV) can be prepared by condensing a sugar oxazoline derivative of the formula (VIII) with a phenylalanine derivative of the formula (IX) in the presence of a suitable catalyst, removing the protecting group, reacting with an acrylamide derivative of the formula (VII) and removal of the protecting group at the sugar moiety.

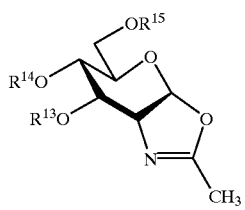

(VIII)

wherein $R^{13}$, $R^{14}$ and $R^{15}$ are each independently acyl-protecting group or ether-protecting group,

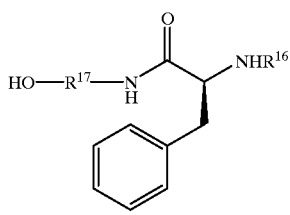

(IX)

wherein $R^{16}$ is a protecting group and $R^{17}$ is alkylene having 2 to 20 carbon atoms,

$$CH_2=CH-CONH-R^{12}-COY \qquad (VII)$$

wherein $R^{12}$ and Y are as defined above,

In the formula (VIII), acyl-protecting group and ether-protecting group are the same as in the formula (V).

In the formula (IX), the protecting group at $R^{16}$ is the same as in the formula (VI). The alkylene at $R^{17}$ and having 2 to 20 carbon atoms is exemplified by ethylene, butylene, hexylene, dodecylene, octadecylene and the like.

Examples of the phenylalanine derivative include N-benzyloxycarbonylphenylalanine-6-hydroxyhexylamide, N-(9-fluorenylmethyloxycarbonyl)-phenylalanine-12-hydroxydodecylamide and the like.

The catalyst to be used for the condensation of a sugar oxazoline derivative and a phenylalanine derivative may be, for example, D-camphour-10-sulfonic acid and the like.

The removal of the protecting group, the reaction with an acrylamide derivative of the formula (VII) and the removal of the protecting group at the sugar moiety can be performed by the method described above.

The prepared polymerizable monomer can be generally purified by column chromatography and the like.

The first step of the present invention aims at binding a sugar residue to the side chain of a water-soluble polymer via a linker having a selectively cleavable linkage to give a primer, and bringing said primer into contact with an immobilized glycosyltransferase in the presence of a sugar nucleotide to transfer the sugar residue of the sugar nucleotide to the sugar residue of said primer.

The transfer of the sugar residue from the sugar nucleotide to the primer polymer is generally done in a neutral buffer containing the above-mentioned primer and the sugar nucleotide, by bringing immobilized glycosyltransferase into contact therewith at 10–60° C., preferably 20–40° C. for 1–120 hr, preferably 2–72 hr.

The reaction mixture may contain a metallic salt as necessary. Examples of the metal ion to be added include magnesium, manganese, cobalt, nickel, copper, zinc and the like, which are generally added in the form of a chloride and the like.

The sugar nucleotide to be used in the present invention is not particularly limited as long as glycosyltransferase can utilize the nucleotide as sugar donor, and may be, for example, uridine-5'-diphosphogalactose, uridine-5'-diphospho-N-acetylglucosamine, uridine-5'-diphospho-N-acetylgalactosamine, uridine-5'-diphosphoglucuronic acid, uridine-5'-diphosphoxylose, guanosine-5'-diphosphofucose, guanosine-5'-diphosphomannose, cytidine-5'-monophospho-N-acetylneuraminic acid and sodium salts thereof.

For example, β1,4-galactosyltransferase can utilize, as sugar donor, uridine 5'-diphosphogalactose analog, such as UDP-4-deoxyglucose, besides uridine-5'-diphosphogalactose (UDP-Gal).

The by-produced nucleotide in the present invention is specifically exemplified by uridine-5'-diphosphate (UDP), guanosine-5'-diphosphate (GDP), cytidine-5'-monophosphate (CMP) and the like produced from sugar nucleotides.

The glycosyltransferase to be used in the present invention may be any as long as it can utilize sugar nucleotide as a sugar doner. Examples of such enzyme include Leloir pathway glycosyltransferase, such as galactosyltransferase, N-acetylglucosaminyltransferase, N-acetylgalactosaminyltransferase, fucosyltransferase, sialyltransferase, mannosyltransferase, xylosyltransferase, glucurononyltransferase and the like.

The immobilized glycosyltransferase to be used in the present invention is free of limitation as long as it is immobilized on a suitable carrier. For example, glycosyltransferase is immobilized by physical adsorption wherein an enzyme is physically adsorbed on a carrier; ionic linkage wherein an enzyme is ionically linked to a carrier having an ion-exchange group; covalent bond method wherein an enzyme is linked to a carrier by covalent bond; crosslinking method wherein enzymes are crosslinked with polyvalent crosslinking agent, followed by insolubilization; inclusion method wherein enzyme is included in a thin lattice of a polymer gel; and other methods. Of these, immobilization by a covalent bond is preferable, since the enzyme leaks less.

The carrier is free of any particular limitation as long as it can (preferably covalently) link an enzyme, and it may be crosslinked dextran, crosslinked agarose and those bonded with an ion-exchange group such as diethylaminoethyl and carboxymethyl. In addition, a commercially available one may be used, such as the above-mentioned carrier previously activated by BrCN treatment, epoxidation, N-hydroxysuccinimidation and the like, which are available for enzyme immobilization and ligand immobilization. The use of such marketed ones makes the preparation of an immobilized enzyme easy.

The second step of the present invention aims at elongation of the sugar chain upon transfer of plural sugar residues by repeating the first step at least once.

The third step of the present invention aims at removal of the by-produced nucleotide and unreacted sugar nucleotide. The method therefor is not particularly limited as long as the primer polymer can be separated from nucleotide and sugar nucleotide. Examples thereof include gel filtration chromatography and the like.

The fourth step of the present invention aims at repeating the first to third steps where necessary, and releasing the glycoconjugate from the above-mentioned primer connecting the sugar chain elongated by the transfer of plural sugar residues, by cleaving at the selectively cleavable linkage contained in the above-mentioned linker. The release of the glycoconjugate from the primer connecting the elongated sugar chain may be done by any method capable of selectively cleaving at the selectively cleavable linkage.

For examples, a primer linked with a group of the formula (I) is brought into contact with ceramide glycanase in a neutral buffer solution at 10–60° C., preferably 20–40° C., for 1–72 hr, preferably 2–24 hr. The reaction mixture may contain a detergent such as Triton CF-54, Triton X-100 and the like. The transfer of sugar chain from the primer to ceramide can be performed by conducting the above-mentioned reaction in the presence of ceramide.

As used herein, the ceramide glycanase refers to the entire enzyme capable of hydrolysis of glycosidic linkage between an oligosaccharide (moiety of sphingoglycolipid) and ceramide, such as commercially available products (e.g., "ceramide glycanase" and "endoglycoceramidase". For example, ceramide glycanase derived from leech and endoglycoceramidase derived from Rhodococcus are used.

One embodiment of the present invention is a production method of sphingoglycolipid, which is characterized by the following steps.

(i) binding a group of the formula (I) to the side chain of a water-soluble polymer via a linker having a selectively cleavable linkage to give a primer, and bringing said primer into contact with an immobilized glycosyltransferase in the presence of a sugar nucleotide, to transfer a sugar residue of said sugar nucleotide to the sugar residue of said primer, (ii) elongating a sugar chain by transfer of plural sugar residues by repeating the step (i) at least once, (iii) removing, where necessary, a by-produced nucleotide or an unreacted sugar nucleotide, and (iv) repeating the steps (i)–(iii) where necessary, and reacting a ceramide glycanase with the primer connecting an elongated sugar chain by the transfer of plural sugar residues in the presence of a ceramide to transfer an oligosaccharide residue having the plural sugar residues to the ceramide.

The ceramide to be used in the present invention may be any as long as it is formed by condensation of fatty acid with sphingosine or its derivative, and one suitable for the sphingoglycolipid to be produced is appropriately selected. Examples of the sphingosine derivative include dihydrosphingosine, phytosphingosine and the like, and examples of the fatty acid include saturated fatty acid, unsaturated fatty acid and α-hydroxy acid, all having 8 to 24 carbon atoms.

The ceramide to be used in the present invention is exemplified by N-stearoylsphingosine (the following formula (k)), N-palmitoylsphingosine, N-lignoceroylsphingosine, N-oleoylsphingosine, N-linoleoylsphingosine, N-alachinoylsphingosine, N-stearoyldihydrosphingosine, N-palmitoyldihydrosphingosine, N-lignoceroyldihydrosphingosine, N-oleoyldihydrosphingosine, N-linoleoyldihydrosphingosine, N-alachinoyldihydrosphingosine, N-stearoylphytosphingosine, N-palmitoylphytosphingosine and the like.

(k)

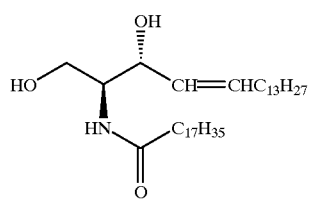

When the group of the formula (II) is linked to the primer, α-chymotrypsin is used instead of ceramide glycanase to release the glycoconjugate from the primer. This step is also carried out as in the case of the above-mentioned ceramide glycanase by contacting with α-chymotrypsin in a neutral buffer at 10–60° C., preferably 20–40° C. for 1–72 hr, preferably 2–24 hr. The reaction mixture may contain calcium chloride and the like as a stabilizer as necessary.

The obtained glycoconjugate can be separated and purified by a conventional method such as column chromatography.

According to the production method of the present invention, glycoconjugates such as oligosaccharide, glycopeptide, glycolipid and the like having an optional sugar chain structure can be quickly obtained with ease by utilizing an immobilized glycosyltransferase.

The present invention is described in more detail in the following by way of examples, to which the present invention is not limited.

REFERENCE EXAMPLE 1

Synthesis of 2-methyl-(3,4,6-tri-O-acetyl-1,2-dideoxy-α-D-glucopyrano)-[2,1-d]-2-oxazoline 2-Acetamido-1,3,4,6-tetra-O-acetyl-2-deoxy-D-glucopyranoside (6.0 g) was dissolved in 1,2-dichloroethane (40 ml) and trimethylsilyl trifluoromethanesulfonate (3.2 ml, hereinafter to be abbreviated as TMSOTf) was added. The mixture was reacted at 50° C. for 7 hr with stirring. After the reaction, the reaction mixture was cooled down to room temperature and triethylamine (10.8 ml) was added. The reaction mixture was concentrated under reduced pressure and applied to silica gel column chromatography (eluent; toluene:ethyl acetate:triethylamine=100:200:1) to give 5.0 g of the objective compound. 2-Methyl-(3,4,6-tri-O-acetyl-1, 2-dideoxy-α-D-glucopyrano)-[2,1-d]-oxazoline had the following structural formula.

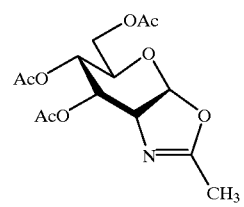

wherein Ac is acetyl.

REFERENCE EXAMPLE 2

Synthesis of N-(benzyloxycarbonylphenylalanyl)-6-amino-1-hexanol

N-Benzyloxycarbonylphenylalanine (11.96 g) and 6-amino-1-hexanol (5.2 g) were dissolved in a mixed solvent (40 ml) of benzene:ethanol=1:1 and N-ethoxycarbonyl-2-ethoxy-1,2-dihydroquinoline (9.9 g, hereinafter to be abbreviated as EEDQ) was added. The mixture was stirred at room temperature for 24 hr. After the reaction, the reaction mixture was concentrated under reduced pressure to dryness, and the residue was recrystallized from benzene to give 13.6 g of the objective compound. N-(Benzyloxycarbonylphenylalanyl)-6-amino-1-hexanol had the following structural formula.

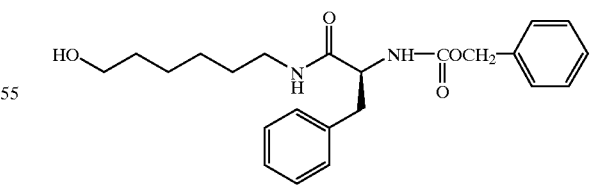

REFERENCE EXAMPLE 3

Synthesis of N-(benzyloxycarbonylphenylalanyl)-6-aminohexyl-2-acetamido-3,4,6-tri-O-acetyl-2-deoxy-β-D-glucopyranoside 2-Methyl-(3,4,6-tri-O-acetyl-1,2-dideoxy-α-D-glucopyrano)-[2,1-d]-2-oxazoline (2.96 g) obtained in Reference Example 1 and N-(benzyloxycarbonylphenylalanyl)-6-amino-1-hexanol (7.17 g) obtained in Reference Example 2 were dissolved in dichloroethane (35 ml), and D-camphour-10-sulfonic acid (hereinafter to be abbreviated as CSA) was added to adjust its pH to 2–3 while keeping the mixture at 70° C. After 30 min, the reaction mixture was cooled down to room temperature, and diluted with chloroform, and the organic layer was washed twice with saturated aqueous sodium hydrogencarbonate solution. The resulting solution was dried over anhydrous magnesium sulfate overnight. Magnesium sulfate was removed by filtration with Celite, and the filtrate was concentrated under reduced pressure. The residual syrup was subjected to silica gel chromatography (mobile phase; chloroform) to give 2.37 g of the objective compound. N-(Benzyloxycarbonylphenylalanyl)-6-aminohexyl-2-acetamido-3,4,6-tri-O-acetyl-2-deoxy-β-D-glucopyranoside had the following structural formula.

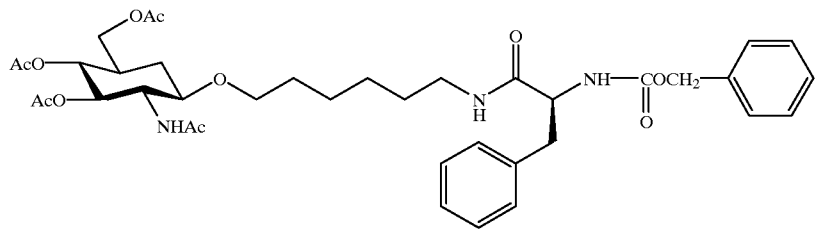

wherein Ac is acetyl.

REFERENCE EXAMPLE 4

Synthesis of 6-acryloylaminocaproic Acid

6-Aminocaproic acid (30.0 g) was dissolved in 1.27M aqueous sodium hydroxide solution (180 ml) and a solution of acryloyl chloride (23.2 ml) in 10 ml of tetrahydrofuran (hereinafter to be abbreviated as THF) was dropwise added under ice-cooling. 4N Aqueous sodium hydroxide solution was added to adjust its pH to 8–9. After the addition, the reaction mixture was gradually warmed to room temperature by stirring for 2 hr. The reaction mixture was adjusted to pH 3 by addition of 1N aqueous hydrochloric acid. The reaction mixture was poured into ice water and extracted with ethyl acetate. The extract was washed with water and dried over anhydrous magnesium sulfate. Magnesium sulfate was filtrated off and the filtrate was concentrated under reduced pressure. The residue was dissolved in a small amount of ethyl acetate and recrystallized from hexane to give 13.0 g of the objective compound. 6-Acryloylaminocaproic acid had the following structural formula.

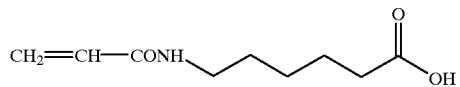

REFERENCE EXAMPLE 5

Synthesis of N-(6'-acryloylaminocaproyl) phenylalanyl-6-aminohexyl-2-acetamido-3,4,6-tri-O-acetyl-2-deoxy-β-D-glucopyranoside N-(Benzyloxycarbonylphenylalanyl)-6-aminohexyl-2-acetamido-3,4,6-tri-O-acetyl-2-deoxy-β-D-glucopyranoside (1.5 g) obtained in Reference Example 3 was dissolved in methanol (40 ml) and 10% palladium-carbon (150 mg) was added, which was followed by stirring at 50° C. for 2 hr under a hydrogen atmosphere. The catalyst was filtered off and the filtrate was concentrated under reduced pressure. The residue and 6-acryloylaminocaproic acid (0.42 g) obtained in Reference Example 4 were dissolved in a mixed solvent of ethanol:benzene=1:1 and EEDQ (0.55 g) was added, which was followed by stirring at room temperature for 24 hr. The reaction mixture was concentrated under reduced pressure and the residue was recrystallized from ethanol to give 1.2 g of the objective compound. N-(6'-Acryloylaminocaproyl)phenylalanyl-6-aminohexyl-2-acetamido-3,4,6-tri-O-acetyl-2-deoxy-β-D-glucopyranoside had the following structural formula.

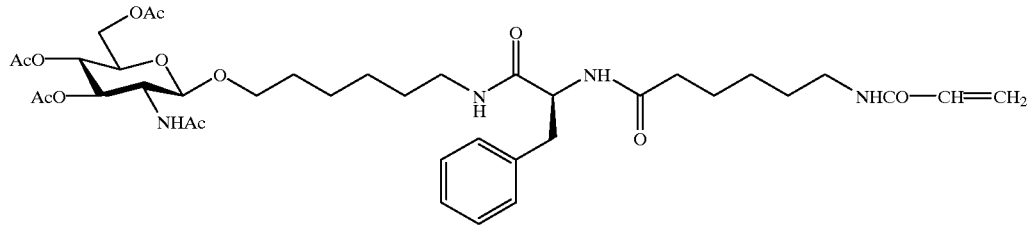

wherein Ac is acetyl.

REFERENCE EXAMPLE 6

Synthesis of N-(6'-acryloylaminocaproyl) phenylalanyl-6-aminohexyl-2-acetamido-2-deoxy-β-D-glucopyranoside N-(6'-Acryloylaminocaproyl)phenylalanyl-6-aminohexyl-2-acetamido-3,4,6-tri-O-acetyl-2-deoxy-β-D-glucopyranoside (590 mg) obtained in Reference Example 5 was dissolved in a mixed solvent (20 ml) of THF:methanol=1:1 and sodium methoxide (16.9 mg) was added, which was followed by stirring at room temperature for 24 hr. An H⁺ type cation exchange resin Dowex 50WX-8 (Dow Chemical) was added to adjust its pH to 7. The ion exchange resin was filtered off, and the filtrate was concentrated under reduced pressure. The residue was recrystallized from a mixed solvent of ethanol:benzene=1:1 to give 413 mg of the objective comound. N-(6'-Acryloylaminocaproyl) phenylalanyl-6-aminohexyl-2-acetamido-2-deoxy-β-D-glucopyranoside had the following structural formula.

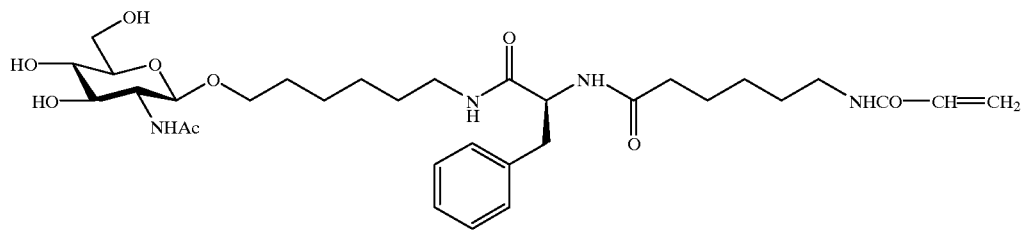

wherein Ac is acetyl.

REFERENCE EXAMPLE 7

Synthesis of N-(6'-acryloylaminocaproyl) phenylalanyl-6-aminohexyl-2-acetamido-2-deoxy-β-D-glucopyranoside-acrylamide Copolymer N-(6'-Acryloylaminocaproyl)phenylalanyl-6-aminohexyl-2-acetamido-2-deoxy-β-D-glucopyranoside (150 mg) obtained in Reference Example 6 was dissolved in 1.5 ml of dimethyl sulfoxide (hereinafter to be abbreviated as DMSO) and a solution of acrylamide (67.2 mg) in water (1 ml) was added. Then, N,N,N',N'-tetramethylethylenediamine (14.3 μl, hereinafter to be abbreviated as TEMED) and ammonium persulfate (8.6 mg) were added to allow copolymerization at 50° C. for 24 hr. The reaction mixture was concentrated under reduced pressure and DMSO was evaporated. The residue was applied to Sephadex G-25 (Pharmacia) column chromatography (mobile phase; 10 mM ammonium acetate) and the eluted fracton containing the objective compound was lyophilized to give 202 mg of the objective compound (molecular weight about 380,000). N-(6'-Acryloylamino-caproyl) phenylalanyl-6-aminohexyl-2-acetamido-2-deoxy-β-D-glucopyranoside residue in the obtained polymer had the following structural formula. The content of above residue was 20 mol %. The H-NMR spectrum of the obtained polymer is shown in FIG. 1.

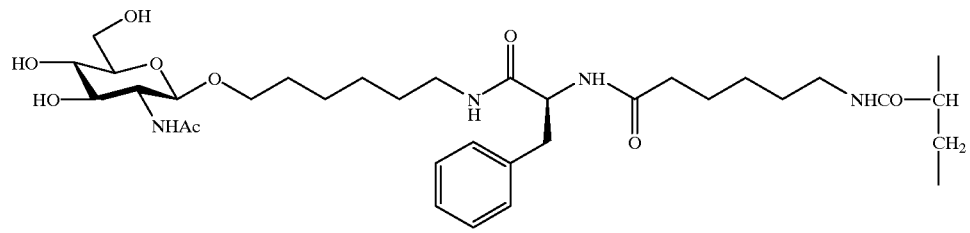

wherein Ac is acetyl.

REFERENCE EXAMPLE 8

Synthesis of N-benzyloxycarbonylserineoctylamide

N-Benzyloxycarbonylserine (12 g) was dissolved in a mixed solvent (120 ml) of ethanol:benzene=1:1 and EEDQ (13.6 g) and n-octylamine (11.1 ml) were added, which was followed by stirring at room temperature overnight. The reaction mixture was concentrated under reduced pressure and recrystallized from toluene to give 12.64 g of the objective compound. N-Benzyloxycarbonylserineoctylamide had the following structural formula.

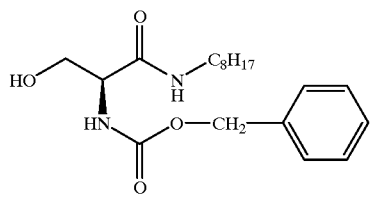

REFERENCE EXAMPLE 9

Synthesis of O-(2,3,6,2',3'4',6'-hepta-O-acetyl) lactosyl-N-benzyloxycarbonylserineoctylamide N-Benzyloxycarbonylserineoctylamide (4.0 g) obtained in Reference Example 8 after thorough drying was dissolved in dichloroethane (80 ml) and activated molecular sieves 4A (8.0 g) and 2,3,6,2',3',4',6'-hepta-O-acetyllactosyl bromide (12.0 g) were added. Silver trifluoromethanesulfonate (4.40 g) was added under ice-cooling and the mixture was gradually warmed to room temperature while stirring overnight under a nitrogen atmosphere. The reaction mixture was filtered with Celite and the filtrate was washed twice with saturated brine and dried over anhydrous magnesium sulfate. After drying, magnesium sulfate was filtered off and the filtrate was concentrated under reduced pressure, which was followed by silica gel column chromatography (mobile phase; toluene:ethyl acetate=5:1) to separate the objective compound. The eluted fraction containing the objective compound was concentrated under reduced pressure to give 5.32 g of the objective compound. O-(2,3,6,2',3',4',6'-hepta-O-Acetyl)lactosyl-N-benzyloxycarbonylserineoctylamide had the following structural formula.

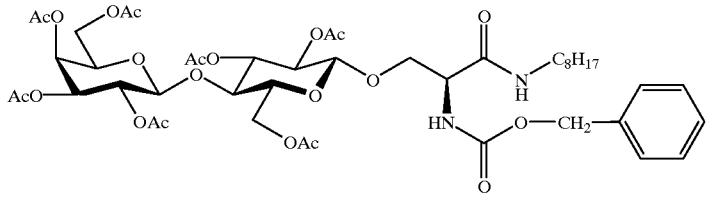

wherein Ac is acetyl.

REFERENCE EXAMPLE 10

Synthesis of O-(2,3,6,2',3',4',6'-hepta-O-acetyl) lactosylserineoctylamide

O-(2,3,6,2',3',4',6'-hepta-O-Acetyl)lactosyl-N-benzyloxycarbonylserineoctylamide (4.0 g) obtained in Reference Example 9 was dissolved in methanol (60 ml) and subjected to catalytic hydrogenation under hydrogen atmosphere at room temperature using 5% palladium-carbon as a catalyst. After the reaction, the catalyst was filtered off and the reaction mixture was concentrated under reduced pressure to give 3.42 g of the objective compound. O-(2,3,6,2',3',4',6'-hepta-O-Acetyl)lactosylserineoctylamide had the following structural formula.

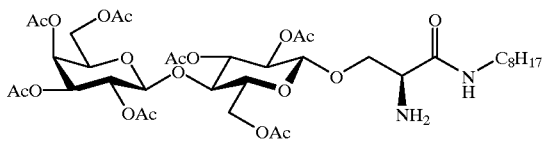

wherein Ac is acetyl.

Reference Example 11

Synthesis of O-(2,3,6,2',3',4',6'-hepta-O-acetyl) lactosyl-N-(6-acryloylamino) caproylserineoctylamide 6-Acryloylaminocaproic acid (278 mg) and EEDQ (371 mg) were added to a mixed solvent (40 ml) of ethanol:benzene=1:1 and thoroughly dissolved. O-(2,3,6,2', 3',4',6'-hepta-O-Acetyl)lactosylserineoctylamide (1.14 g) obtained in Reference Example 10 was added and the mixture was stirred at room temperature overnight. The reaction mixture was concentrated under reduced pressure and the residue was purified by silica gel chromatography (mobile phase; chloroform:methanol=100:1). The eluate containing the objective compound was concentrated under reduced pressure to give 1.06 g of the objective compound. O-(2,3,6,2',3',4',6'-hepta-O-Acetyl)lactosyl-N-(6-acryloylamino)caproylserineoctylamide had the following structural formula.

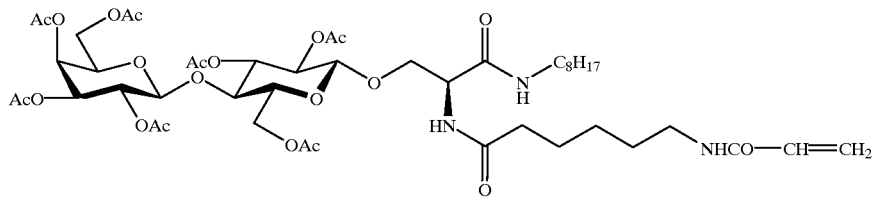

wherein Ac is acetyl.

REFERENCE EXAMPLE 12

Synthesis of O-lactosyl-N-(6-acryloylamino) caproylserineoctylamide

O-(2,3,6,2',3',4',6'-hepta-O-Acetyl)lactosyl-N-(6-acryloylamino)caproylserineoctylamide (400 mg) obtained in Reference Example 11 was dissolved in a mixed solvent of tetrahydrofuran:methanol=1:1, and sodium methoxide (8.49 mg) was added, which was followed by stirring at room temperature for 2 hr. An $H^+$ type cation exchange resin Dowex 50W (Dow Chemical) was added to neutralize the solution. The ion exchange resin was filtered off and the filtrate was concentrated under reduced pressure. The residue was recrystallized from ethanol to give 270 mg of the objective compound. O-Lactosyl-N-(6-acryloylamino) caproylserineoctylamide had the following structural formula.

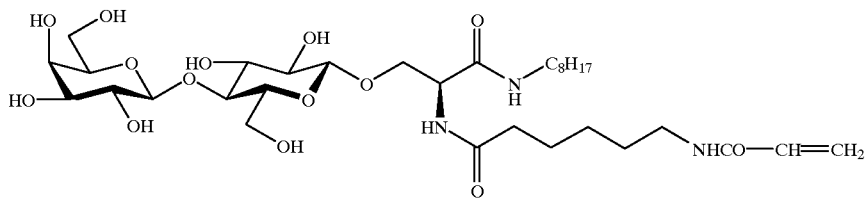

REFERENCE EXAMPLE 13

Synthesis of O-lactosyl-N-(6-acryloylamino) caproylserineoctylamide-acrylamide Copolymer O-Lactosyl-N-(6-acryloylamino)caproylserineoctylamide (150 mg) obtained in Reference Example 12 and acrylamide (60.25 mg) were dissolved in 2 ml of a mixed solvent of DMSO:water=1:1, and TEMED (12 µl) and ammonium persulfate (7.67 mg) were added, which was followed by polymerization at 50° C. overnight. The objective compound was purified by Sephadex G-25 (Pharmacia) column chromatography equilibrated with distilled water. The eluate containing the objective compound was lyophilized to give 200 mg of the objective compound (molecular weight about 500,000). O-Lactosyl-N-(6-acryloylamino) caproylserineoctylamide residue in the obtained polymer had the following structural formula. The content of above residue was 20 mol %.

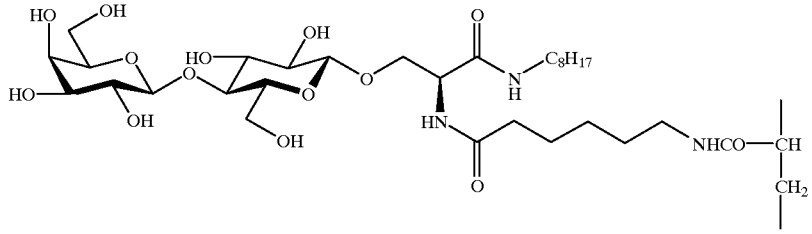

REFERENCE EXAMPLE 14

Preparation of Immobilized β1,4-galactosyltransferase

CNBr activated Sepharose 4B (0.5 g, Pharmacia) was taken and washed three times with 1 mM HCl (total 100 ml). Thereto were added β1,4-galactosyltransferase derived from milk (Sigma, 5U), uridine-5'-diphosphogalactose (1 mM, hereinafter to be abbreviated as UDP-Gal), N-acetylglucosamine (5 mM), manganese chloride (25 mM) and 0.1 M borate buffer (5 ml, pH 8.0) containing NaCl (0.5 M), and the mixture was gently stirred by shaking at 4° C. overnight. The immobilized β1,4-galactosyltransferase was filtered off through glass filter and washed with the above-mentioned buffer (5 ml) without β1,4-galactosyltransferase. 0.1 M Tris-HCl buffer (5 ml, pH 8.0) was added and the unreacted activated site on the carrier was blocked. The immobilized enzyme was washed with 1 M aqueous sodium chloride solution and water, immersed in 25 mM cacodylate buffer (pH 7.4) containing UDP-Gal (1 mM) and manganese chloride (5 mM) and stored at 4° C.

REFERENCE EXAMPLE 15

Preparation of Immobilized α2,3-sialyltransferase

CNBr activated Sepharose 4B (0.5 g, Pharmacia) was taken and washed three times with 1 mM HCl (total 100 ml). Thereto were added α2,3-sialyltransferase (1U) derived from swine liver and 0.1 M borate buffer (5 ml, pH 8.0) containing cytidine-5'-diphosphate (1 mM), and the mixture was gently stirred by shaking at 4° C. overnight. The immobilized α2,3-sialyltransferase was filtered off through glass filter and washed with the above-mentioned buffer (5 ml) without α2,3-sialyltransferase. The unreacted activated site on the carrier was blocked in the same manner as in Reference Example 14. After washing, α2,3-sialyltransferase was immersed in 25 mM cacodylate buffer (pH 7.4) containing cytidine-5'-monophospho-N-acetylneuraminic acid (1 mM, hereinafter to be abbreviated as CMP-NeuAc) and stored at 4° C.

REFERENCE EXAMPLE 16

Preparation of Immobilized α2,6-sialyltransferase

In the same manner as in Reference Example 15 except that rat liver-derived α2,6-sialyltransferase (0.5 U) instead of α2,3-sialyltransferase (1U) to prepare the objective compound, which was stored at 4° C.

EXAMPLE 1

Transfer of Galactose to Primer by Immobilized β1,4-galactosyltransferase

Figure 2:
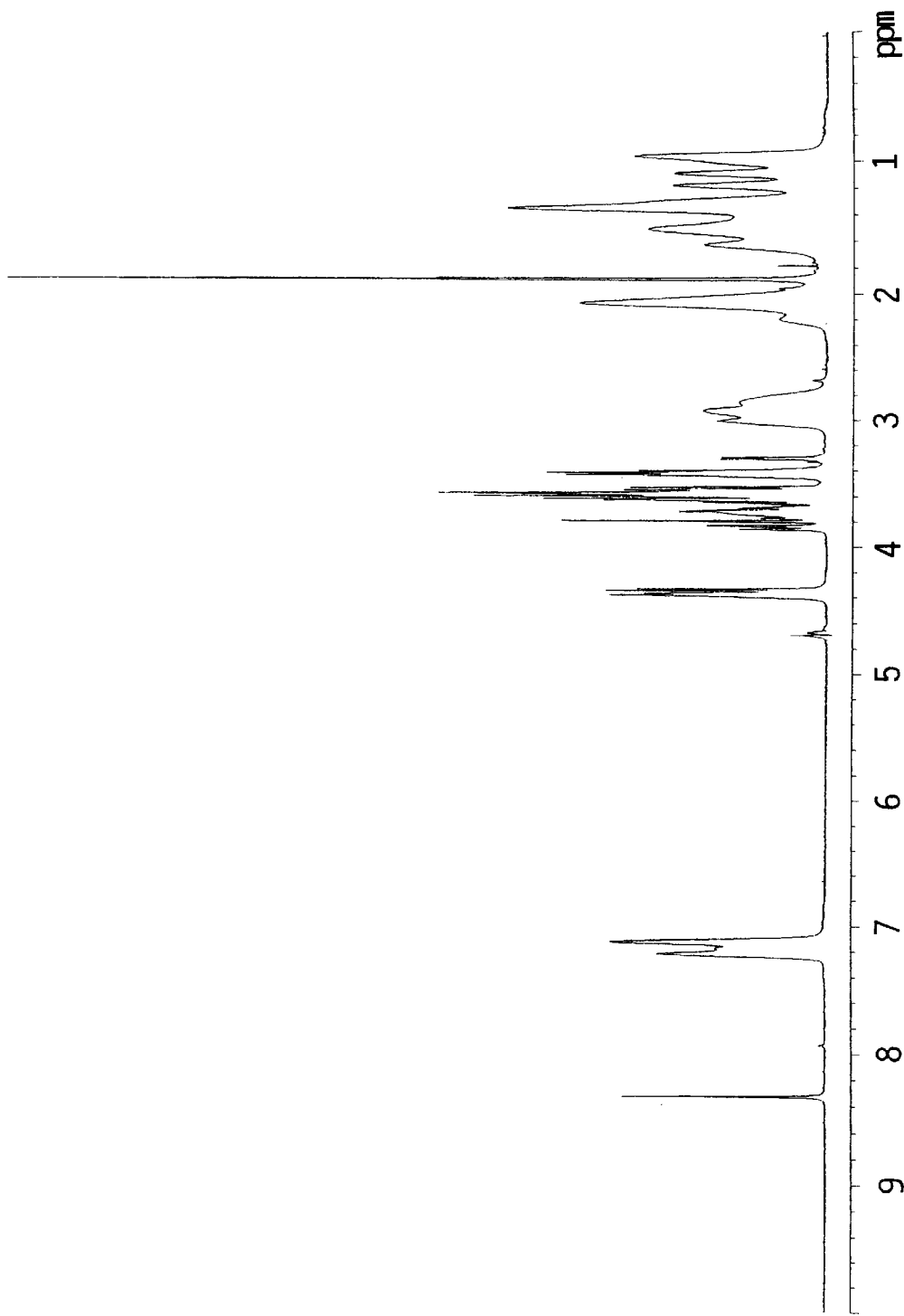
FIG. 2 is an H-NMR spectrum chart of the product having transferred galactose (Example 1).

To 50 mM HEPES (1 ml, pH 6.0) containing N-(acryloylaminocaproyl)-phenylalanyl-6-aminohexyl-2-acetamido-2-deoxy-β-D-glucopyranoside-acrylamide copolymer (40 mg) obtained in Reference Example 7, UDP-Gal (32 mg), manganese chloride (10 mM) and α-lactalbumin (0.26 mg/ml) was added immobilized β1,4-galactosyltransferase (1 ml) obtained in Reference Example 14 and the mixture was allowed to react at 37° C. for 48 hr. After the reaction, immobilized β1,4-galactosyltransferase was removed by centrifugation, and the product was purified by Sephadex G-25 (Pharmacia) column chromatography (mobile phase; 50 mM ammonium formate), which was followed by lyophilization to give 37 mg of the product. The H-NMR spectrum of above product showed occurrence of galactose transfer. The H-NMR spectrum is shown in FIG. 2. The N-(6'-acryloylaminocaproyl)-phenylalanyl-6-aminohexyl-2-acetamido-2-deoxy-β-D-glucopyranoside residue in the polymer, to which galactose had transferred, had the following structural formula.

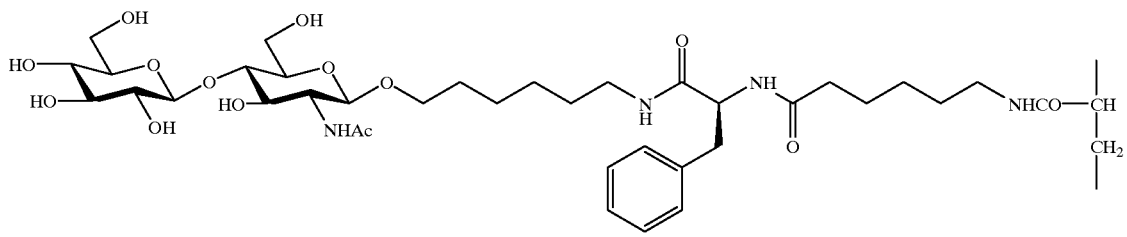

wherein Ac is acetyl.

EXAMPLE 2

Transfer of N-acetylneuraminic Acid to Primer by Immobilized α2,6-sialyltransferase To 50 mM sodium cacodylate buffer (2 ml, pH 7.4) containing the primer (30 mg) to which galactose had transferred, as obtained in Example 1, CMP-NeuAc (30 mg), bovine serum albumin (1 mg), manganese chloride (1.2 mg), and alkaline phosphatase (20 U) derived from calf was added immobilized α2,6-sialyltransferase (1 ml) obtained in Reference Example 16 and the mixture was reacted at 37° C. for 72 hr. After the reaction, 28 mg of a product was obtained in the same manner as in Example 1. The H-NMR spectrum of above product showed occurrence of transfer of N-acetylneuraminic acid. The N-(6'-acryloylaminocaproyl)-phenylalanyl-6-aminohexyl-2-acetamido-2-deoxy-β-D-glucopyranoside residue in the polymer, to which galactose and then N-acetylneuraminic acid had transferred, had the following structural formula.

EXAMPLE 3

Transfer of N-acetylneuraminic Acid to Primer by Immobilized α2,3-sialyltransferase To 50 mM sodium cacodylate buffer (2 ml, pH 7.4) containing O-lactosyl-N-(6-acryloylamino)caproylserineoctylamide-acrylamide copolymer (30 mg) obtained in Reference Example 13, CMP-NeuAc (30 mg), bovine serum albumin (8 mg), manganese chloride (1.2 mg) and alkaline phosphatase (20 U) derived from calf was added immobilized α2,3-sialyltransferase (1 ml) obtained in Reference Example 15, and the mixture was reacted at 37° C. for 72 hr. After the reaction, immobilized α2,3-sialyltransferase was removed by centrifugation, and the product was purified by Sephadex G-25 (Pharmacia) column chromatography (mobile phase; 50 mM ammonium formate), which was followed by lyophilization to give 27 mg of the product. The H-NMR spectrum of above product showed occurrence of transfer of N-acetylneuraminic acid. The O-lactosyl-N-(6-acryloylamino)-caproylserineoctylamide residue in the polymer, to which N-acetylneuraminic acid had transferred, had the following structural formula.

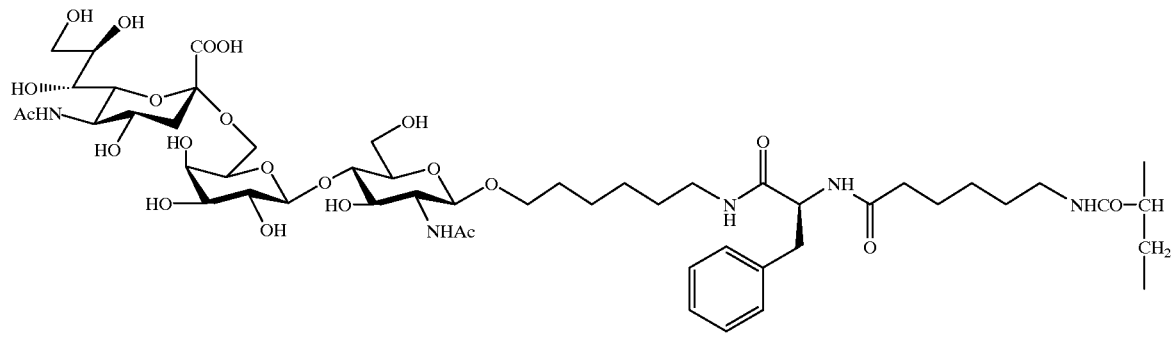

wherein Ac is acetyl.

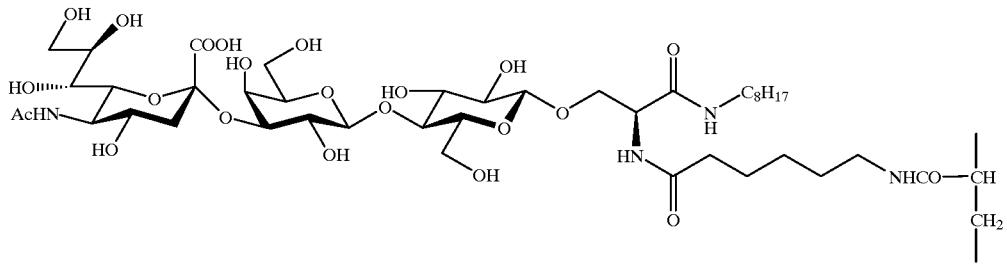

wherein Ac is acetyl.

EXAMPLE 4

Cleaving Out of Glycoconjugate From Primer With α-chymotrypsin

The polymer (20 mg) obtained in Example 2 and α-chymotrypsin (0.6 mg) were dissolved in 80 mM Tris-hydrochloric acid buffer (2 ml, pH 7.8, containing 0.1 M calcium chloride) and the mixture was reacted at 40° C. for 24 hr. The product was purified by Sephadex G-25 (Pharmacia) column chromatography (mobile phase; 50 mM ammonium formate) to separate the product fraction, which was followed by lyophilization to give 18 mg of the product. The obtained product was identified as compound having the following structural formula by H-NMR spectrum.

wherein Ac is acetyl.

EXAMPLE 5

Transfer of Sugar Chain to N-stearoylsphingosine From Primer by Ceramide Glycanase To 50 mM citrate buffer (1 ml, pH 6.0) containing the polymer (20 mg) obtained in Example 3, N-stearoylsphingosine (50 mg) and Triton CF-54 (20 μl) was added leech-derived ceramide glycanase (0.01 U), and the mixture was reacted at 37° C. for 17 hr. After the reaction, the product was separated by Sephadex LH-20 (Pharmacia) column chromatography equilibrated with chloroform:methanol:water=60:30:5. The eluate containing the product was concentrated to dryness under reduced pressure to give 18 mg of the product. Analysis by HPLC confirmed that the product was 1-O-(N-acetylneuraminyl-α-(2→3))lactosyl-N-stearoylsphingosine. 1-O-(N-Acetylneuraminyl-α-(2→3))lactosyl-N-stearoylsphingosine has the following structural formula.

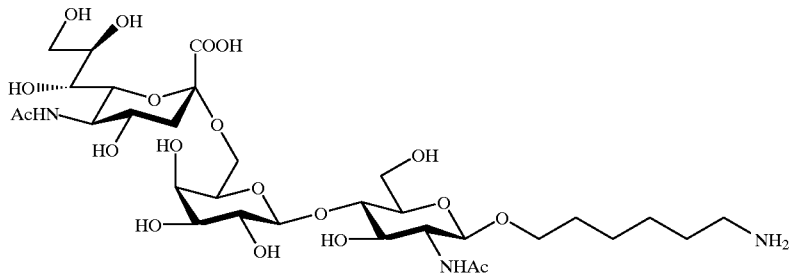

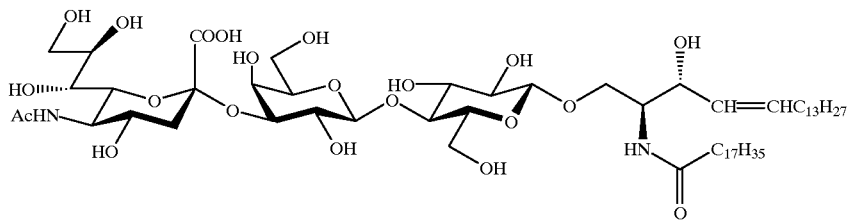

wherein Ac is acetyl.

This application is based on application No. 203443/1997 filed in Japan, the content of which is incorporated hereinto by reference.

What is claimed is:

1. A method for producing glycoconjugate, which comprises the steps of:
   (i) binding a sugar residue to a side chain of a water-soluble polymer via a linker having a selectively cleavable linkage to give a primer, and bringing said primer into contact with an immobilized glycosyltransferase in the presence of a sugar nucleotide, to transfer a sugar residue of said sugar nucleotide to the sugar residue of said primer;
   (ii) elongating a sugar chain by transfer of a plurality of sugar residues by repeating step (i) at least once;
   (iii) optionally removing a by-produced nucleotide or an unreacted sugar nucleotide;
   (iv) optionally repeating steps (i)–(iii); and
   (v) optionally releasing the resultant glycoconjugate sugar chain by selectively cleaving the cleavable linkage in the linker from the primer, which connects the sugar chain elongated by the transfer of the plurality of sugar residues.

2. The method of claim 1, wherein the water-soluble polymer is a polymer or a copolymer of acrylic or methacrylic monomers of acrylic acid, methacrylic acid, acrylamide, methacrylamide and derivatives thereof, or a copolymer of an acrylic or methacrylic monomer and a different vinyl compound.

3. The method of claim 1, wherein the selectively cleavable linkage in the linker can be cleaved by hydrolase in an aqueous solvent.

4. The method of claim 1, wherein the selectively cleavable linkage in the linker can be cleaved by protease or ceramide glycanase in an aqueous solvent.

5. The method of claim 1, wherein the water-soluble polymer having a sugar residue linked to its side chain via a linker having a selectively cleavable linkage is a water-soluble polymer having a group of the formula (I) or formula (II) linked to its side chain:

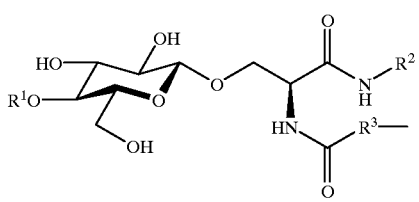
(I)

wherein $R^1$ is a β-galactose residue or H, $R^2$ is alkyl or alkenyl having 6 to 20 carbon atoms and $R^3$ is alkylene having 5 to 19 carbon atoms,

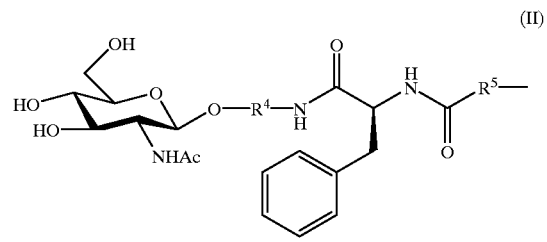
(II)

wherein $R^4$ is alkylene having 2 to 20 carbon atoms, $R^5$ is alkylene having 5 to 19 carbon atoms and Ac is acetyl.

6. The method of claim 1, wherein the immobilized glycosyltransferase is a glycosyltransferase immobilized onto a carrier by a covalent bond.

7. The method of claim 1, wherein the carrier is a crosslinked dextran or a crosslinked agarose with or without an ion-exchange group linked thereto.

8. A method for producing a sphingoglycolipid, which comprises the steps of:
   (i) binding a group of the formula (I) to a side chain of a water-soluble polymer to give a primer, and bringing said primer into contact with an immobilized glycosyltransferase in the presence of a sugar nucleotide, to transfer a sugar residue of said sugar nucleotide to the sugar residue of said primer,

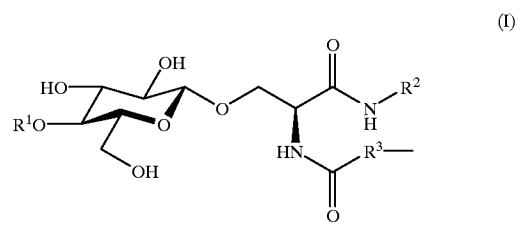
(I)

wherein $R^1$ is a β-galactose residue or H, $R^2$ is alkyl or alkenyl having 6 to 20 carbon atoms and $R^3$ is alkylene having 5 to 19 carbon atoms;
   (ii) elongating a sugar chain by transfer of a plurality of sugar residues by repeating step (i) at least once;
   (iii) optionally removing a by-produced nucleotide or an unreacted sugar nucleotide; and
   (iv) optionally repeating steps (i)–(iii); and
   (v) reacting a ceramide glycanase with the primer in the presence of a ceramide, wherein an oligosaccharide comprising the plurality of sugar residues is transferred from the primer to the ceramide.

* * * * *